US008826910B2

(12) United States Patent
Kwok et al.

(10) Patent No.: US 8,826,910 B2
(45) Date of Patent: Sep. 9, 2014

(54) MASK AND VENT ASSEMBLY THEREFOR

(71) Applicant: ResMed Limited, Bella Vista (AU)

(72) Inventors: Philip Rodney Kwok, Chatswood (AU); Perry David Lithgow, Moruya (AU)

(73) Assignee: ResMed Limited, Bella Vista (AU)

(*) Notice: Subject to any disclaimer, the term of this patent is extended or adjusted under 35 U.S.C. 154(b) by 0 days.

(21) Appl. No.: 13/764,401

(22) Filed: Feb. 11, 2013

(65) Prior Publication Data
US 2013/0152369 A1    Jun. 20, 2013

Related U.S. Application Data

(63) Continuation of application No. 12/944,583, filed on Nov. 11, 2010, which is a continuation of application No. 10/298,845, filed on Nov. 19, 2002, now Pat. No. 7,845,354, which is a continuation of application No. 09/452,558, filed on Dec. 1, 1999, now Pat. No. 6,561,191, which is a continuation-in-part of application No. 09/021,541, filed on Feb. 10, 1998, now Pat. No. 6,561,190.

(30) Foreign Application Priority Data

Feb. 10, 1997 (AU) ..................................... PO5045

(51) Int. Cl.
| A62B 7/10 | (2006.01) |
| B23P 11/02 | (2006.01) |
| A61M 16/06 | (2006.01) |
| A62B 18/02 | (2006.01) |
| A62B 18/10 | (2006.01) |

(52) U.S. Cl.
CPC ............ *B23P 11/02* (2013.01); *A61M 2205/42* (2013.01); *A61M 16/06* (2013.01); *A61M 16/0683* (2013.01); *A62B 18/02* (2013.01); *A62B 18/10* (2013.01)
USPC ................................ 128/207.12; 128/206.21

(58) Field of Classification Search
CPC ........ A62B 18/18; A62B 18/00; A62B 18/10; A62B 18/02; A62B 18/025; A62B 18/08; A61M 2205/42; A61M 16/06; A61M 16/0605; A61M 16/20; A61M 16/208; A61M 2016/06
USPC ........................................ 128/206.21–207.13
See application file for complete search history.

(56) References Cited

U.S. PATENT DOCUMENTS

| 781,516 A | 1/1905 | Guthrie |
| 812,706 A | 2/1906 | Warbasse |

(Continued)

FOREIGN PATENT DOCUMENTS

| AU | 91/77110 B | 11/1991 |
| AU | 94/64816 B | 12/1994 |

(Continued)

OTHER PUBLICATIONS

Communication issued in a Corresponding European Application No. 10 182 727.7, dated Dec. 19, 2012.
Office Action in a corresponding U.S. Appl. No. 12/944,583, dated Feb. 12, 2013.

(Continued)

*Primary Examiner* — Rachel Young
(74) *Attorney, Agent, or Firm* — Nixon & Vanderhye P.C.

(57) ABSTRACT

A method for attaching a removable, washout vent insert to a CPAP mask, the CPAP mask comprised of a rigid plastics shell having an inlet tube, the rigid plastics shell having an opening bounded by a rim, the vent insert being made of a material more flexible than the rigid plastic shell, the vent insert having a plurality of orifices, the vent insert, in a cross-sectional view, having a recess located at its periphery, includes: squeezing the vent insert along its longitudinal axis; aligning the vent insert so it is oriented to match the shape of the opening; inserting the vent insert into the opening; and releasing the vent insert once it is within the opening, the vent insert resiliently expanding to engage the rim of the opening.

24 Claims, 4 Drawing Sheets

(56) References Cited

U.S. PATENT DOCUMENTS

| | | | |
|---|---|---|---|
| 835,075 A | 11/1906 | Mahaffy | |
| 1,081,745 A | 12/1913 | Johnston et al. | |
| 1,192,186 A | 7/1916 | Greene | |
| 1,653,572 A | 12/1927 | Jackson | |
| 1,926,027 A | 9/1933 | Biggs | |
| 2,008,677 A | 7/1935 | Booharin | |
| 2,102,037 A | 12/1937 | Schwartz | |
| 2,123,353 A | 7/1938 | Catt | |
| 2,248,477 A | 7/1941 | Lombard | |
| 2,254,854 A | 9/1941 | O'Connell | |
| 2,259,817 A | 10/1941 | Hawkins | |
| 2,317,608 A | 9/1943 | Heidbrink | |
| 2,371,965 A | 3/1945 | Lehmberg | |
| 2,376,871 A | 5/1945 | Fink | |
| 2,415,846 A | 2/1947 | Randall | |
| 2,438,058 A | 3/1948 | Kincheloe | |
| 2,578,621 A | 12/1951 | Yant | |
| 2,843,121 A | 7/1958 | Hudson | |
| 2,872,923 A | 2/1959 | Birch et al. | |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,162,411 A | 12/1964 | Duggan | |
| 3,182,659 A | 5/1965 | Blount | |
| 3,189,027 A | 6/1965 | Bartlett | |
| 3,238,943 A | 3/1966 | Holley | |
| 3,291,127 A | 12/1966 | Eimer et al. | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,395,701 A | 8/1968 | Bartlett, Jr. et al. | |
| 3,412,231 A | 11/1968 | McElligott | |
| 3,490,452 A | 1/1970 | Greenfield | |
| 3,513,844 A | 5/1970 | Smith | |
| 3,556,122 A | 1/1971 | Laerdal | |
| 3,580,051 A | 5/1971 | Blevins | |
| 3,680,556 A | 8/1972 | Morgan | |
| 3,700,000 A | 10/1972 | Hesse et al. | |
| 3,720,235 A | 3/1973 | Schrock | |
| 3,762,747 A | 10/1973 | Grifen | |
| 3,796,216 A | 3/1974 | Schwarz | |
| 3,799,164 A | 3/1974 | Rollins | |
| D231,803 S | 6/1974 | Huddy | |
| 3,850,171 A | 11/1974 | Ball et al. | |
| 3,866,095 A | 2/1975 | Marmorek | |
| 3,868,164 A | 2/1975 | Lisk | |
| 3,877,425 A | 4/1975 | O'Neill | |
| 3,889,671 A | 6/1975 | Baker | |
| 3,942,403 A | 3/1976 | Pramberger | |
| 3,949,743 A | 4/1976 | Shanbrom | |
| 3,958,275 A | 5/1976 | Morgan et al. | |
| 4,037,142 A | 7/1977 | Poole | |
| 4,077,404 A | 3/1978 | Elam | |
| D250,131 S | 10/1978 | Lewis et al. | |
| 4,137,602 A | 2/1979 | Klumpp, Jr. | |
| 4,167,185 A | 9/1979 | Lewis | |
| 4,201,205 A | 5/1980 | Bartholomew | |
| 4,219,020 A | 8/1980 | Czajka | |
| 4,226,234 A | 10/1980 | Gunderson | |
| 4,245,632 A | 1/1981 | Houston | |
| 4,258,710 A | 3/1981 | Reber | |
| 4,266,540 A | 5/1981 | Panzik et al. | |
| 4,274,406 A | 6/1981 | Bartholomew | |
| 4,276,877 A | 7/1981 | Gdulla | |
| D262,322 S | 12/1981 | Mizerak | |
| 4,304,229 A | 12/1981 | Curtin | |
| 4,328,797 A | 5/1982 | Rollins, III et al. | |
| 4,347,205 A | 8/1982 | Stewart | |
| 4,354,488 A | 10/1982 | Bartos | |
| 4,363,580 A | 12/1982 | Bell | |
| 4,402,316 A | 9/1983 | Gadberry | |
| 4,408,818 A | 10/1983 | Markarian | |
| 4,412,537 A | 11/1983 | Tiger | |
| 4,440,163 A | 4/1984 | Spergel | |
| 4,454,881 A | 6/1984 | Huber et al. | |
| 4,467,799 A | 8/1984 | Steinberg | |
| 4,522,639 A | 6/1985 | Ansite et al. | |
| 4,535,767 A | 8/1985 | Tiep et al. | |
| 4,558,710 A | 12/1985 | Eichler | |
| 4,559,939 A | 12/1985 | Levine et al. | |
| 4,580,556 A | 4/1986 | Kondur | |
| 4,601,465 A | 7/1986 | Roy | |
| 4,616,647 A | 10/1986 | McCreadie | |
| 4,622,964 A | 11/1986 | Flynn | |
| 4,648,394 A | 3/1987 | Wise | |
| 4,649,912 A | 3/1987 | Collins | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| D293,613 S | 1/1988 | Wingler | |
| 4,739,755 A | 4/1988 | White et al. | |
| 4,770,169 A | 9/1988 | Schmoegner et al. | |
| 4,774,941 A | 10/1988 | Cook | |
| 4,774,946 A | 10/1988 | Ackerman | |
| 4,782,832 A | 11/1988 | Trimble et al. | |
| 4,799,477 A | 1/1989 | Lewis | |
| 4,809,692 A | 3/1989 | Nowacki et al. | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,915,105 A | 4/1990 | Lee | |
| 4,919,128 A | 4/1990 | Kopala et al. | |
| 4,938,210 A | 7/1990 | Shene | |
| 4,938,212 A | 7/1990 | Snook et al. | |
| 4,944,310 A | 7/1990 | Sullivan | |
| D310,431 S | 9/1990 | Bellm | |
| 4,969,901 A | 11/1990 | Binder | |
| 4,971,051 A | 11/1990 | Toffolon | |
| 4,974,586 A | 12/1990 | Wandel et al. | |
| 4,986,269 A | 1/1991 | Hakkinen | |
| 4,989,596 A | 2/1991 | Macris et al. | |
| 4,989,599 A | 2/1991 | Carter | |
| 5,005,568 A | 4/1991 | Loescher et al. | |
| 5,005,571 A | 4/1991 | Dietz | |
| 5,018,519 A | 5/1991 | Brown | |
| 5,038,776 A | 8/1991 | Harrison et al. | |
| 5,042,473 A | 8/1991 | Lewis | |
| 5,042,478 A * | 8/1991 | Kopala et al. | 128/207.18 |
| 5,046,200 A | 9/1991 | Feder | |
| 5,046,512 A | 9/1991 | Murchie | |
| 5,063,922 A | 11/1991 | Hakkinen | |
| 5,065,756 A | 11/1991 | Rapoport | |
| D322,318 S | 12/1991 | Sullivan | |
| 5,069,205 A | 12/1991 | Urso | |
| 5,069,222 A | 12/1991 | McDonald, Jr. | |
| 5,069,586 A | 12/1991 | Casey | |
| 5,080,094 A | 1/1992 | Tayebi | |
| D323,908 S | 2/1992 | Hollister et al. | |
| 5,109,839 A | 5/1992 | Blasdell et al. | |
| 5,109,840 A | 5/1992 | Daleiden | |
| 5,117,819 A | 6/1992 | Servidio et al. | |
| 5,121,745 A | 6/1992 | Israel | |
| 5,133,347 A | 7/1992 | Huennebeck | |
| 5,140,982 A | 8/1992 | Bauman | |
| 5,148,802 A | 9/1992 | Sanders et al. | |
| 5,159,938 A | 11/1992 | Laughlin | |
| 5,178,138 A | 1/1993 | Walstrom et al. | |
| D334,633 S | 4/1993 | Rudolph | |
| 5,231,983 A | 8/1993 | Matson et al. | |
| 5,233,978 A | 8/1993 | Callaway | |
| 5,243,971 A | 9/1993 | Sullivan | |
| 5,245,995 A | 9/1993 | Sullivan et al. | |
| 5,265,595 A | 11/1993 | Rudolph | |
| 5,269,296 A | 12/1993 | Landis | |
| 5,279,289 A | 1/1994 | Kirk | |
| 5,280,784 A | 1/1994 | Kohler | |

(56) References Cited

U.S. PATENT DOCUMENTS

| | | | |
|---|---|---|---|
| 5,297,544 A | 3/1994 | May | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,357,951 A | 10/1994 | Ratner | |
| 5,358,340 A | 10/1994 | Bober | |
| 5,368,020 A | 11/1994 | Beux | |
| 5,372,130 A | 12/1994 | Stern et al. | |
| 5,388,571 A | 2/1995 | Roberts et al. | |
| 5,404,871 A | 4/1995 | Goodman et al. | |
| 5,411,193 A * | 5/1995 | Culp | 224/669 |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,474,060 A | 12/1995 | Evans | |
| 5,477,852 A | 12/1995 | Landis et al. | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,533,506 A | 7/1996 | Wood | |
| 5,538,000 A | 7/1996 | Rudolph | |
| 5,540,223 A | 7/1996 | Starr et al. | |
| 5,542,128 A | 8/1996 | Lomas | |
| RE35,339 E | 10/1996 | Rapoport | |
| 5,560,354 A | 10/1996 | Berthon-Jones et al. | |
| 5,570,682 A | 11/1996 | Johnson | |
| 5,570,689 A | 11/1996 | Starr et al. | |
| 5,575,277 A | 11/1996 | Lutz et al. | |
| D377,089 S | 12/1996 | Starr et al. | |
| 5,586,551 A | 12/1996 | Hilliard | |
| 5,592,938 A | 1/1997 | Scarberry et al. | |
| 5,608,647 A | 3/1997 | Rubsamen et al. | |
| 5,642,730 A | 7/1997 | Baran | |
| 5,645,049 A | 7/1997 | Foley et al. | |
| 5,647,355 A | 7/1997 | Starr et al. | |
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A * | 8/1997 | Landis et al. | 128/207.13 |
| 5,660,566 A | 8/1997 | Ohsumi | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,709,204 A | 1/1998 | Lester | |
| 5,715,741 A | 2/1998 | Gasser et al. | |
| 5,715,814 A | 2/1998 | Ebers | |
| 5,724,965 A | 3/1998 | Handke et al. | |
| 5,732,695 A | 3/1998 | Metzger | |
| 5,746,201 A | 5/1998 | Kidd | |
| 5,765,553 A | 6/1998 | Richards et al. | |
| 5,813,423 A | 9/1998 | Kirchgeorg | |
| 5,832,918 A | 11/1998 | Pantino | |
| 5,836,303 A | 11/1998 | Hurst et al. | |
| 5,839,433 A | 11/1998 | Higenbottam | |
| 5,857,460 A | 1/1999 | Popitz | |
| 5,878,742 A | 3/1999 | Figueredo et al. | |
| 5,897,396 A | 4/1999 | Maejima | |
| 5,921,239 A | 7/1999 | McCall et al. | |
| 5,924,420 A | 7/1999 | Reischel et al. | |
| 5,937,851 A | 8/1999 | Serowski et al. | |
| 6,006,748 A | 12/1999 | Hollis | |
| 6,012,455 A | 1/2000 | Goldstein | |
| 6,019,101 A | 2/2000 | Cotner et al. | |
| 6,039,044 A | 3/2000 | Sullivan | |
| 6,083,141 A | 7/2000 | Hougen | |
| 6,112,746 A | 9/2000 | Kwok et al. | |
| 6,119,693 A | 9/2000 | Kwok et al. | |
| 6,119,694 A | 9/2000 | Correa et al. | |
| 6,135,109 A | 10/2000 | Blasdell et al. | |
| 6,192,886 B1 | 2/2001 | Rudolph | |
| 6,309,438 B1 | 10/2001 | Kanno et al. | |
| 6,431,172 B1 | 8/2002 | Bordewick | |
| 6,435,181 B1 | 8/2002 | Jones et al. | |
| 6,478,026 B1 | 11/2002 | Wood | |
| 6,491,034 B1 | 12/2002 | Gunaratnam et al. | |
| 6,561,190 B1 | 5/2003 | Kwok | |
| 6,561,191 B1 | 5/2003 | Kwok | |
| 6,581,594 B1 | 6/2003 | Drew et al. | |
| 6,584,976 B2 | 7/2003 | Japuntich et al. | |
| 6,595,215 B2 | 7/2003 | Wood | |
| 6,644,316 B2 | 11/2003 | Bowman et al. | |
| 6,668,830 B1 | 12/2003 | Hansen et al. | |
| 6,792,623 B2 | 9/2004 | Luppi | |
| 6,823,865 B2 | 11/2004 | Drew et al. | |
| 7,159,587 B2 | 1/2007 | Drew et al. | |
| 7,207,335 B2 | 4/2007 | Kwok | |
| 7,845,354 B2 | 12/2010 | Kwok et al. | |
| 2002/0162558 A1 | 11/2002 | Noble | |
| 2003/0079751 A1 | 5/2003 | Kwok | |
| 2003/0116160 A1 | 6/2003 | Kwok et al. | |
| 2003/0172936 A1 | 9/2003 | Wilkie et al. | |
| 2004/0065327 A1 | 4/2004 | Gradon et al. | |
| 2004/0065330 A1 | 4/2004 | Landis | |
| 2004/0182397 A1 | 9/2004 | Wood | |
| 2004/0226566 A1 | 11/2004 | Gunaratnam et al. | |
| 2004/0261797 A1 | 12/2004 | White | |
| 2005/0011524 A1 | 1/2005 | Thomlinson | |
| 2005/0028821 A1 | 2/2005 | Wood | |
| 2005/0028822 A1 | 2/2005 | Sleeper | |
| 2005/0051177 A1 | 3/2005 | Wood | |
| 2005/0076913 A1 | 4/2005 | Ho | |
| 2005/0092326 A1 | 5/2005 | Drew et al. | |
| 2005/0199242 A1 | 9/2005 | Matula | |
| 2006/0196509 A1 | 9/2006 | Drew et al. | |
| 2011/0162651 A1 | 7/2011 | Drew et al. | |
| 2011/0277771 A1 | 11/2011 | Kwok et al. | |

FOREIGN PATENT DOCUMENTS

| | | |
|---|---|---|
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| AU | 712236 | 4/1999 |
| CA | 1039144 | 9/1978 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0601708 | 6/1994 |
| EP | 0 608 684 A1 | 8/1994 |
| EP | 0 658 356 | 6/1995 |
| EP | 0697 225 A2 | 7/1995 |
| EP | 0 697 255 A | 2/1996 |
| EP | 178 925 A2 | 4/1996 |
| EP | 0 747 078 A2 | 12/1996 |
| EP | 0 821 978 | 2/1998 |

(56) References Cited

FOREIGN PATENT DOCUMENTS

| | | |
|---|---|---|
| EP | 1 027 905 A | 8/2000 |
| EP | 1163923 A2 | 6/2001 |
| FR | 2 574 657 A1 | 6/1986 |
| FR | 2 658 725 A1 | 8/1991 |
| FR | 2 749 176 | 12/1997 |
| GB | 799 225 | 8/1958 |
| GB | 1 395 391 | 5/1975 |
| GB | 1 467 828 | 3/1977 |
| GB | 2 106 396 | 4/1983 |
| GB | 2145335 A | 3/1985 |
| GB | 2147506 A | 5/1985 |
| GB | 2 164 569 A | 3/1986 |
| GB | 2 236 681 A | 4/1991 |
| GB | 2 267 648 A | 12/1993 |
| GB | 2 354 953 | 4/2001 |
| JP | 52-76695 | 12/1950 |
| JP | 463702 | 5/1971 |
| JP | 463703 | 6/1971 |
| JP | 57-1477 | 11/1982 |
| JP | 63105772 | 5/1988 |
| JP | H1-172845 | 12/1989 |
| JP | 02-000191 | 1/1990 |
| JP | 2-141775 | 11/1990 |
| JP | 7000521 | 1/1995 |
| JP | 9010311 | 1/1997 |
| JP | 09-087919 | 3/1997 |
| JP | 09/216240 A | 8/1997 |
| JP | A-11-267234 | 10/1999 |
| JP | A-2000-140587 | 5/2000 |
| JP | 2000-279520 | 10/2000 |
| JP | 2001-511035 | 8/2001 |
| JP | 2001-333982 | 12/2001 |
| JP | 2002-95751 | 4/2002 |
| JP | 2004-535226 | 11/2004 |
| WO | WO 80/01044 | 5/1980 |
| WO | WO 82/03548 | 10/1982 |
| WO | WO 84/01293 | 4/1984 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/28207 | 9/1996 |
| WO | WO 96/39206 | 12/1996 |
| WO | WO 97/07847 | 3/1997 |
| WO | WO 97/41911 | 11/1997 |
| WO | WO 97/46281 | 12/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/04842 | 2/1999 |
| WO | WO 00/13751 | 3/2000 |
| WO | WO 00/74758 | 12/2000 |
| WO | WO 01/26722 | 4/2001 |
| WO | WO 01/32250 | 5/2001 |
| WO | WO 01/89381 | 11/2001 |
| WO | WO 01/97892 | 12/2001 |
| WO | WO 02/096342 | 12/2002 |
| WO | WO 03/076020 | 9/2003 |
| WO | WO 2004/073778 | 9/2004 |
| WO | WO 2005/063328 | 7/2005 |
| WO | WO 2005/079726 | 9/2005 |

OTHER PUBLICATIONS

Mask 1 Photographs, Respironics Inc. Reusable Full Mask (small) Part #452033 Lot #951108.
Mask 2 Photographs, Puritan—Bennett, Adam Curcuit, Shell Part #231700, Swivel Part #616329-00, Pillows (medium) Part #616324.
Mask 3 Photographs, DeVilbiss Healthcare Inc., DeVilbiss Seal-Ring and CPAP Mask Kit (medium), Part 73510-669.
Mask 4 Photographs, Respironics Inc., Monarch Mini Mask with Pressure Port, Part #572004, Monarch Headgear, Part #572011.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, DeVilbiss Healthcare Inc., Small Mask and Seal-Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironics Inc., Soft Cap (medium), Part #302142.
Mask 11 Photographs, Weinmann: Hamburg, Nasalmaskensystem mit Schallampfer (medium), Part #WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.
PCT International Search Report, PCT/AU2004/000207 (Apr. 28, 2004).
PCT International Search Report, PCT/AU2005/000515 (Jun. 2, 2005).
PCT International Preliminary Report on Patentability, PCT/AU2005/000515 (Oct. 11, 2006), 8 pgs.
U.S. Appl. No. 11/645,582, Kwok, filed Dec. 27, 2006.
Instruction Brochure for "E-vent-N" Aug. 1997, © Dräger Medizintechnik GmbH, 2 pages.
Translation of Official Action for Japanese Patent Application No. 2001-381410 issued Jun. 6, 2007 (2 pages).
Office Action in Japanese Appln. No. 2004-197875 (Oct. 9, 2007) with English translation.
English Translation of Japanese Office Action, Jan. 6, 2004, 3 pages.
European Office Action, Feb. 16, 2004, 2 pages.
Japanese Office Action issued in JP Appln. No. 2001-381410 (Feb. 17, 2009) with English translation.
Supplemental European Search Report issued in EP Appln. No. 05729503 (Nov. 9, 2009).
Second Office Action issued in Chinese Appln. No. 200580012190.8, issued Feb. 5, 2010.
European Search Report for European Appln. 10182727.7, mailed Dec. 20, 2010, 6 pages.
European Search Report for corresponding European Appln. 10183335.8, mailed Dec. 28, 2010, 7 pages.
Extend Search Report issued in related European Appln. 10183335.8 (Apr. 13, 2011).
Preliminary Notice of Rejection and English Translation for corresponding Japanese Application No. 2010-181667, mailed Jul. 10, 2012, 8 pages.
Final Office Action issued in a corresponding Japanese Appl. No. 2010-181667 with English translation thereof, dated May 7, 2013.
Office Action issued in a corresponding Japanese Application No. 2012-254330 dated Oct. 29, 2013, with English language translation thereof.
Summons to Attend Oral Hearing Proceedings issued in corresponding European Appln. No. 10182727.7 dated Feb. 11, 2014.

\* cited by examiner

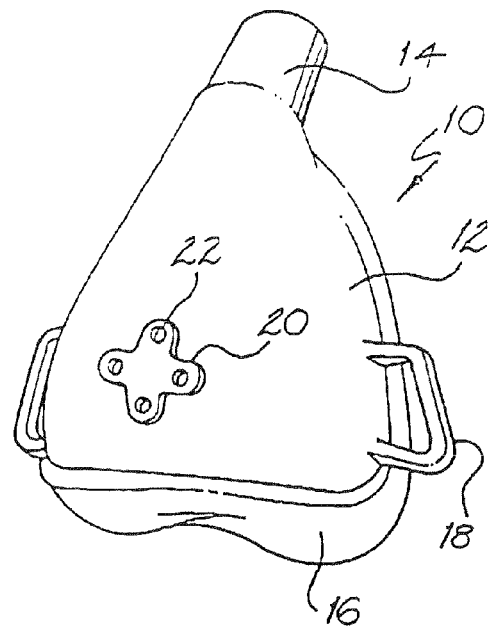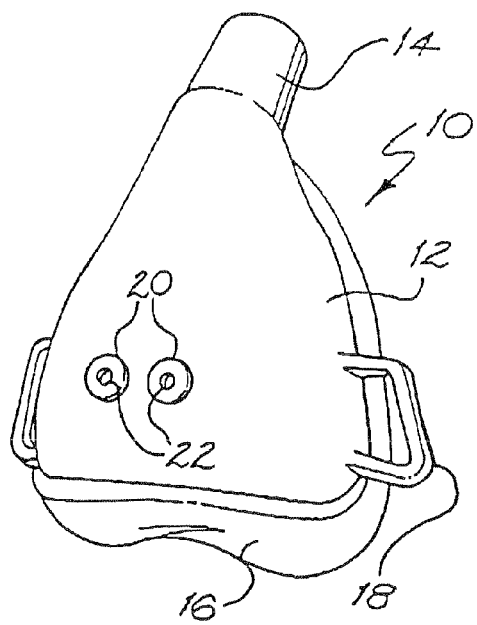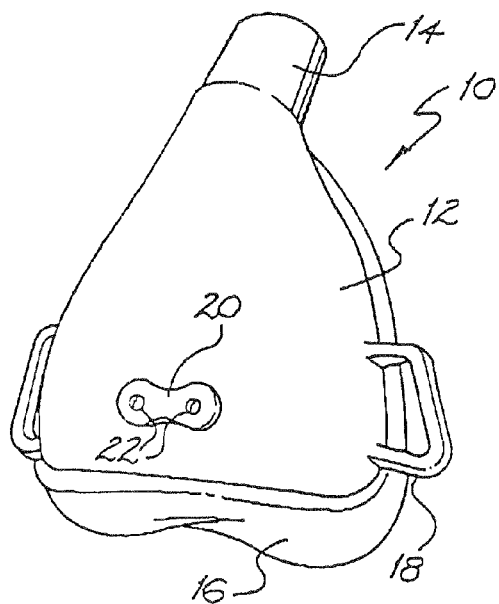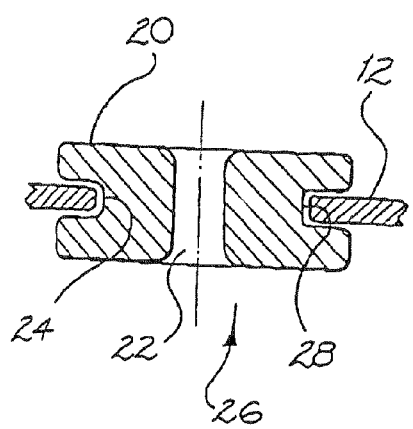

MASK AND VENT ASSEMBLY THEREFOR

CROSS REFERENCE TO RELATED APPLICATIONS

This application is a continuation of U.S. patent application Ser. No. 12/944,583, filed Nov. 11, 2012, which is a continuation of U.S. patent application Ser. No. 10/298,845, filed Nov. 19, 2002, now U.S. Pat. No. 7,845,354, which is a continuation of U.S. application Ser. No. 09/452,558, filed Dec. 1, 1999, now U.S. Pat. No. 6,561,191, which is a continuation-in-part of application Ser. No. 09/021,541, filed Feb. 10, 1998, now U.S. Pat No. 6,561,190, which claims the priority of Australian Application No. PO5045, filed Feb. 10, 1997, each of which is incorporated herein by reference in its entirety.

FIELD OF THE INVENTION

The present invention relates to a mask and a vent assembly therefor.

The mask and vent assembly according to the invention have been developed primarily for the venting of washout gas in the application of continuous positive airway pressure (CPAP) Treatment in conjunction with a system for supplying breathable gas pressurised above atmospheric pressure to a human or animal. Such a system is used, for example, in the treatment of obstructive sleep apnea (OSA) and similar sleep disordered breathing conditions. However, the invention is also suitable for other purposes including, for example, the application of assisted ventilation or respiration.

The term "mask" is herein intended to include face masks, nose masks, mouth masks, nasal pillows, appendages in the vicinity of any of these devices and the like.

BACKGROUND OF THE INVENTION

Treatment of OSA by CPAP flow generator systems involves the continuous delivery of air (or other breathable gas) pressurised above atmospheric pressure to a patient's airways via a conduit and a mask.

For either the treatment of OSA or the application of assisted ventilation, the pressure of the gas delivered to a patient can be at a constant level, bi-level (ie. in synchronism with patient inspiration and expiration) or automatically adjusting in level to match therapeutic need. Throughout this specification the reference to CPAP is intended to incorporate a reference to any one of, or combinations of, these forms of pressure delivery.

The masks used in CPAP treatment generally include a vent for washout of the gas to atmosphere. The vent is normally located in the mask or in the gas delivery conduit adjacent the mask. The washout of gas through the vent is essential for removal of exhaled gases from the breathing circuit to prevent carbon dioxide "re-breathing" or build-up, both of which represent a health risk to the mask wearer. Adequate gas washout is achieved by selecting a vent size and configuration that will allow a minimum safe gas flow at the lowest operating CPAP pressure, which, typically can be as low as around 4 cm $H_2O$ for adults and 2 cm $H_2O$ in paediatric applications.

Prior art masks are generally comprised of a rigid plastic shell which covers the wearer's nose and/or mouth. A flexible or resilient rim (or cushion) is attached to the periphery of the shell which abuts and seals against the wearer's face to provide a gas-tight seal around the nose and/or mouth.

A prior art washout vent utilized one or more holes or slits in the rigid shell or in a rigid portion of the delivery conduit to allow the washout gas to vent to atmosphere. In some masks, the holes or slits were formed during the moulding process. In others, they were drilled or cut as a separate step after the shell or conduit had been moulded.

The flow of gas out the holes or slits in the shell or conduit to atmosphere creates noise and turbulence at the hole or slit outlet as the delivered gas, and upon expiration, the patient-expired gas (including $CO_2$) exits. Bi-level and autosetting gas delivery regimes tend to generate more noise than a constant level gas delivery regime. This is thought to be due to the extra turbulence created by the gas accelerating and decelerating as it cycles between relatively low and relatively high pressures. The noise adversely affects patient and bed-partner comfort.

Another prior art vent included hollow rivets or plugs manufactured from stainless steel or other rigid materials attached to openings in the rigid shell. The outer edges of the rivets were rounded to help reduce noise. However, this approach was expensive, required an extra production step and did not prove effective in reducing noise.

Another approach to reduce noise involved the use of sintered filters at the gas outlet of the mask shell. However, the filters were prone to blocking, especially in the presence of moisture. Accordingly, sintered filters were impractical for use in CPAP treatment as they were easily blocked by the moisture from the patient's respiratory system or humidifiers or during the necessary regular cleaning of the mask and associated componentry.

Foam filters wrapped around the air outlets in the shell were also attempted. However, they also suffered from the disadvantages of being prone to blocking, difficult to clean and requiring constant replacement.

Remote outlet tubes have been used to distance the noise source from the patient. However, these tubes are difficult to clean, are prone to entanglement by the patient and/or their bed partner and suffer the further disadvantage that a volume of exhausted gas is retained in the tube adjacent the mask.

It is an object of the present invention to substantially overcome or at least ameliorate the prior art disadvantages and, in particular, to reduce the noise generated by gas washout through a mask.

SUMMARY OF THE INVENTION

Accordingly, the invention, in a first aspect, discloses a mask for use with a system for supplying breathable gas pressurised above atmospheric pressure to a human or animal's airways, the mask includes a mask shell which is, in use, in fluid communication with a RIS supply conduit; and a gas washout vent assembly, the gas washout vent assembly includes at least one gas washout orifice extending from a first side of the vent assembly positioned, in use, adjacent the human or animal's face and a second side positioned, in use, adjacent the atmosphere and the cross-sectional area of the orifice at the first side is larger than the cross-sectional area of the orifice at the second side.

In a second aspect, the invention discloses a vent assembly for the washout of gas from a mask or conduit used with a system for supplying breathable gas pressurized above atmospheric pressure to a human or animal, the vent assembly includes at least one gas washout orifice extending from a first side of the vent assembly placed, in use, adjacent the human or animal's face to a second side placed, in use, adjacent the atmosphere, the cross-sectional area of the orifice at the first side is larger than the cross-sectional area of the orifice at the second side.

Preferably, the orifice includes a first substantially cylindrical portion adjacent the first side, a second cylindrical portion adjacent the second side and a tapering portion between the first and second substantially cylindrical portions.

Preferably also, the second substantially cylindrical portion and the tapering portion are of approximately equal thickness in the axial direction of the orifice and are thicker than the first substantially cylindrical portion.

Desirably, the vent assembly includes a plurality of said orifices therethrough.

Desirably also, each of said orifices is separated from the other(s) of said orifices by at least the diameter of the orifice at the second side.

BRIEF DESCRIPTION OF THE DRAWINGS

Preferred embodiments of the invention will now be described, by way of examples only, with reference to the accompanying drawings in which:

FIG. 5 is a perspective view of a fifth embodiment;
FIG. 6 is a perspective view of a sixth embodiment;
FIG. 7 is a perspective view of a seventh embodiment;
FIG. 8 is a partial cross-sectional view of the first embodiment along the line 8-8 of FIG. 1.

DESCRIPTION OF THE PREFERRED EMBODIMENTS

Figure 1:
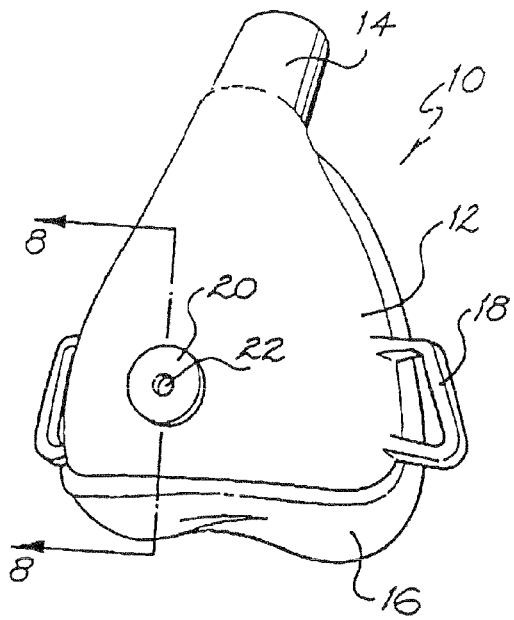
FIG. 1 is a perspective view of a first embodiment.
Figure 2:
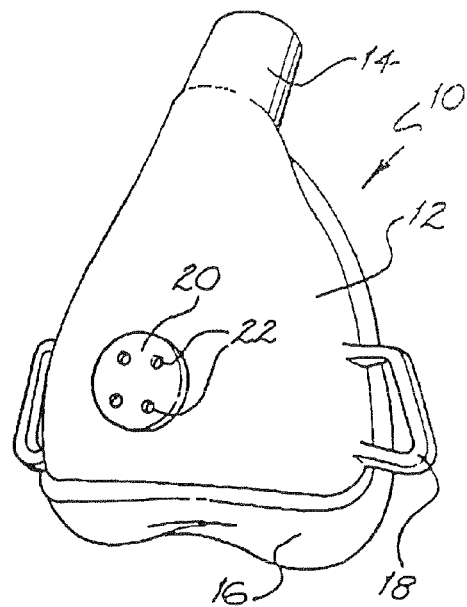
FIG. 2 is a perspective view of a second embodiment.

Referring firstly to FIG. 1, there is shown a mask 10 for use with a system (not shown) for supplying breathable gas pressurised above atmospheric pressure to a human or animal's airways. The mask includes a rigid plastics shell 12 having an inlet tube 14 for connection to a supply conduit to communicate breathable gas from a flow generator (not shown) to the nasal passages of the mask wearer. The mask shell 12 also includes a flexible sealing membrane 16 which is used to provide a gas tight seal between the face of the wearer and the interior of the shell 12. The shell 12 also includes lugs 18 for connecting the mask 10 to a head strap (not shown) to retain the mask in place.

The mask includes a Silastic™ insert 20 through which is provided an orifice 22 for gas washout. As best shown in FIG. 8, the insert 20 has a recess or groove 24 around its periphery. A correspondingly sized opening 26 bounded by a rim 28 is provided in the shell 12 to enable the insert 20 to be retained in place in the fashion of a grommet. The opening 26 can be moulded in the shell 12 or drilled or punched as a post-moulding step. The flexibility of the Silastic™ allows the insert 20 to be initially squeezed through the opening 26 before resiliently expanding to the configuration shown in FIG. 8 and engaging the rim 28.

FIGS. 2 to 7 show further embodiments in which corresponding reference numerals are used to indicate like features. In all these embodiments the insert 20 has an external groove or recess 24 which engages the rim 28 of a corresponding shaped opening 26 in the mask shell 12 to retain the insert 20 in place.

In the embodiment shown in FIGS. 2 to 5 and 7 the insert 20 includes more than one orifice 22. In the embodiment shown in FIG. 6, two inserts 20 are provided in the shell 12.

Figure 9:
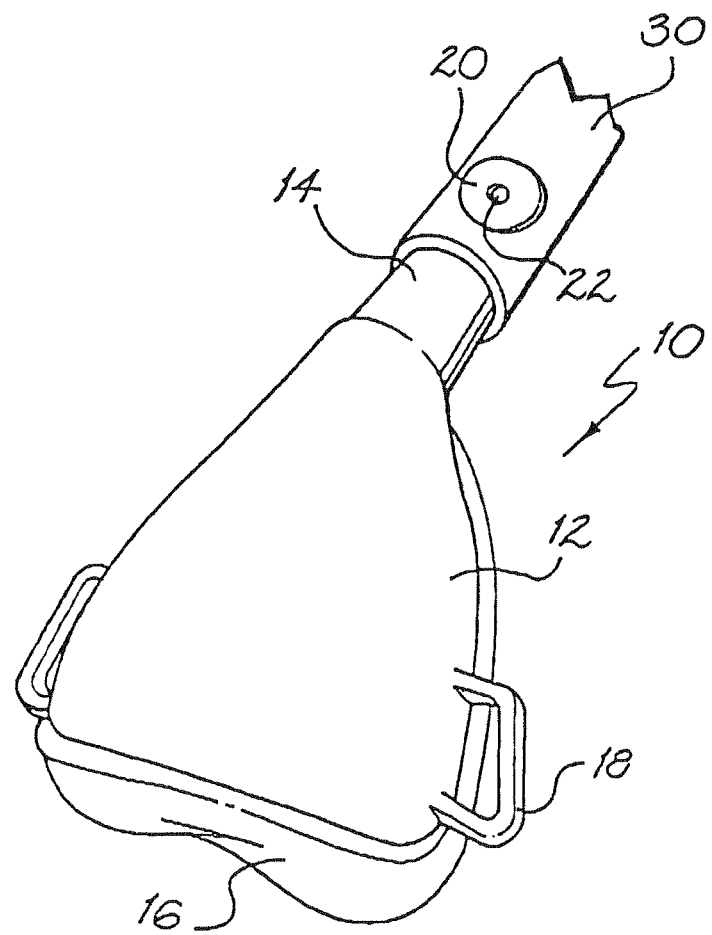
FIG. 9 is a perspective view of an eighth embodiment.

In the embodiment shown in FIG. 9, the insert 20 is provided in a gas supply conduit 30.

Figure 3:
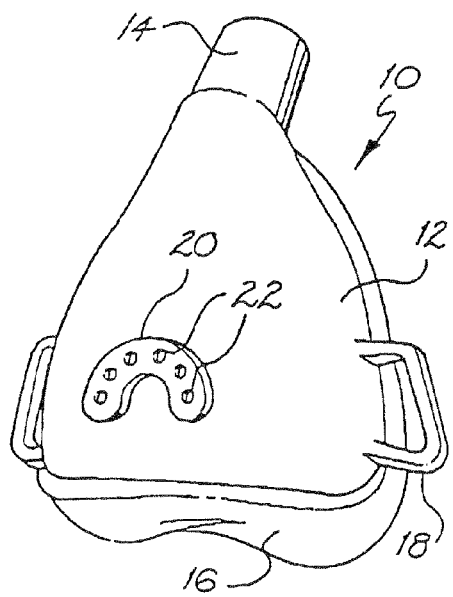
FIG. 3 is a perspective view of a third embodiment.
Figure 4:
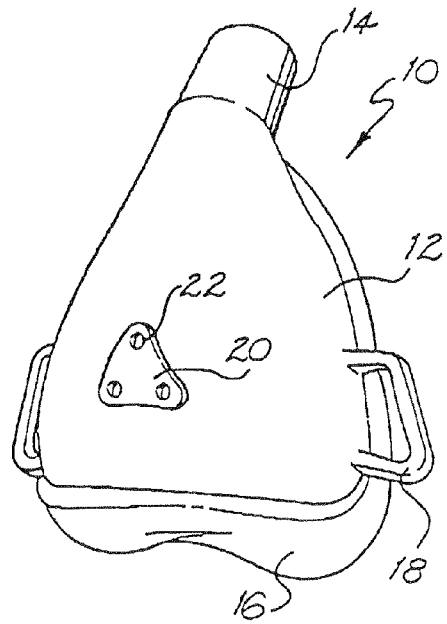
FIG. 4 is a perspective view of a fourth embodiment.
Figure 10:
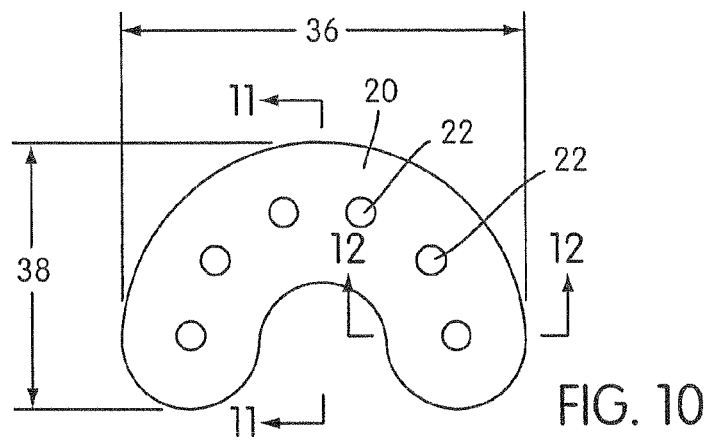
FIG. 10 is a plan view of the insert of the third embodiment.
Figure 11:
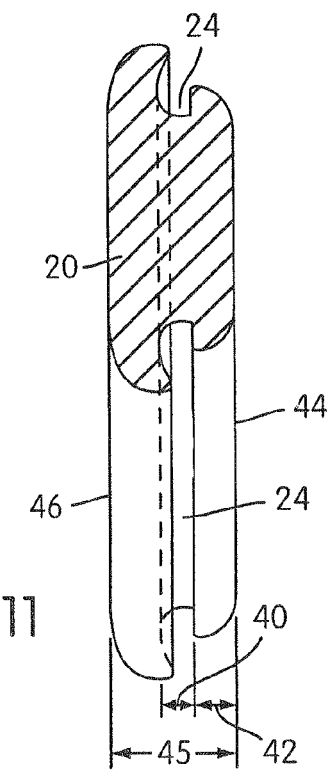
FIG. 11 is a cross-sectional view of the third embodiment insert along the line 11-11 of FIG. 10.
Figure 12:
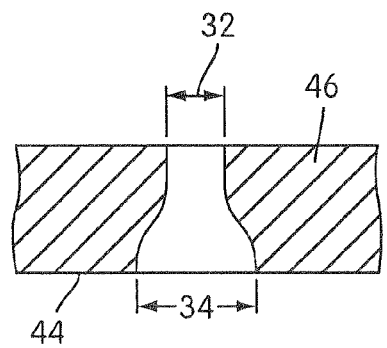
FIG. 12 is a partial cross-sectional view of the third embodiment insert along the line 12-12 of FIG. 10.

FIGS. 10 to 12 show the insert 20 of the third embodiment of FIG. 3. The dimensions 32, 34, 36, 38, 40, 42 and 45 are approximately diameter 1.73 mm, diameter 3.30 mm, 28.80 mm, 19.00 mm, 1.20 mm, 1.20 mm and 3.60 mm respectively.

The side 44 of the insert 20 faces the patient's face in use and the side 46 faces atmosphere.

The mask shell 12 is manufactured from polycarbonate. Other rigid plastics materials can equally be used. The insert 20 can be manufactured from an elastomer sold as Silastic™ (produced by the Dow Corning Corporation) or a thermoplastic elastomer sold as Santoprene™ (produced by Monsanto). Other flexible elastomeric materials can be used also.

The mask 10 produces less noise than an identical mask having a similar sized and shaped orifice(s) formed directly in the mask shell 12 instead of formed in the flexible insert 20. It is thought that the noise reduction occurs due to the flexible insert 20 damping vibrations caused by air passage through the orifice(s) 22 which produce vibrations or similar in the mask shell 12.

A prototype of the embodiment of the invention shown in FIG. 3 has been tested over a range of constant and bi-level CPAP treatment pressures. For comparison purposes, an identical mask to that shown in FIG. 3 but formed entirely from polycarbonate and having six identical arcuately spaced holes 22 drilled directly through the mask shell was also tested. In both masks the six holes had a diameter of 1.7 mm. The results of the test are summarised in the Tables below:

TABLE 1

| Constant level gas delivery | | |
|---|---|---|
| Pressure | Noise levels 1 m from mask (dBA) | |
| (cm H$_2$O) | With flexible insert | Without flexible insert |
| 4 | 26.8 | 35.2 |
| 10 | 33.4 | 43.1 |
| 18 | 39.3 | 49.2 |

TABLE 2

| Bi-level gas delivery | | |
|---|---|---|
| Pressure | Noise levels 1 m from mask (dBA) | |
| (cm H$_2$O) | With flexible insert | Without flexible insert |
| 5-10 | 30.8-38.5 | 37.2-43.0 |
| 10-15 | 38.6-43.7 | 42.9-47.9 |

As the results show, the mask shown in FIG. 3 produced less radiated noise than a similar mask not including the flexible elastomeric insert 20 representing a significant advantage in terms of the comfort of the mask wearer and their bed partner.

In addition to the noise reduction discussed above, the masks 10 possesses other advantages over those of the prior art. Firstly, the insert 20 is very easy to install into the mask shell 12 during either assembly of the mask which, is often supplied in kit form, or before and after cleaning which is regularly required and often carried out in the home environment. Secondly, the mask shell 12 may be produced with a single size of opening 26 and provided with a range of different inserts 20 which allows the outlet size to be "tuned" to give an optimum gas washout rate for a particular patient's treatment pressure level.

Although the invention has been described with reference to specific examples, it will be appreciated by those skilled in the art, that the invention may be embodied in many other forms.

We claim:

1. A method for attaching a removable, washout vent insert to a CPAP mask, the CPAP mask comprised of a shell having an inlet tube, the CPAP mask comprising polycarbonate material, the shell having only a single opening for purposes of $CO_2$ washout, the single opening being bounded by a rim of said polycarbonate material, the vent insert being made of a material more flexible than the polycarbonate material of the rim, the vent insert having a plurality of orifices to continuously exhaust $CO_2$-laden gas from the CPAP mask during the entire breathing cycle of a patient while reducing noise generated by gas washout, the vent insert, in a cross-sectional view, having an inner flange and an outer flange, the inner and outer flanges defining a recess therebetween at a periphery of the vent insert, the method comprising:
    squeezing the vent insert;
    aligning the vent insert so it is oriented to match the shape of the single opening in the CPAP mask;
    inserting the inner flange of the vent insert into the single opening; and
    releasing the vent insert once the inner flange is within the single opening, the vent insert resiliently expanding to receive the rim in the recess, engage the inner flange with an inner surface of the rim, and engage the outer flange with an outer surface of the rim,
    wherein an outer end of each orifice at an outer exit side of the insert is positioned outward of the outer surface of the rim,
    wherein the recess of the vent insert and the single opening have non-circular, complementary shapes,
    wherein a cross-sectional area of each orifice at an inner entry side of the vent insert is larger than a cross-sectional area of each orifice at the outer exit side of the vent insert, and
    wherein the vent insert is insertable into the single opening in only a single orientation in which a smaller end of each orifice is positioned at the outer exit side of the vent insert.

2. The method of claim 1, wherein the outer flange of the insert, as seen in cross-section, includes first and second flange portions on opposing sides of the insert to receive the rim on opposing sides of the single opening, and the first and second flange portions on each side of the insert extend a substantially equal distance from the single opening.

3. The method of claim 1, wherein the vent insert is structured to continuously exhaust gas in the range of 4-18 $cmH_2O$.

4. A method for attaching a washout vent insert to a CPAP mask, the CPAP mask comprised of a shell having an inlet tube, the CPAP mask having only a single opening for purposes of $CO_2$ washout, the single opening being bounded by a rim, the vent insert having a plurality of orifices to continuously exhaust $CO_2$-laden gas from the CPAP mask during the entire breathing cycle of a patient, the vent insert structured and configured to reduce noise during gas washout, the vent insert having an inner flange and an outer flange, the inner and outer flanges defining a recess therebetween at a periphery of the vent insert, the method comprising:
    squeezing the vent insert;
    aligning the vent insert so it is oriented to match the shape of the single opening in the CPAP mask;
    inserting the inner flange of the vent insert into the single opening; and
    releasing the vent insert once the inner flange is within the single opening, the vent insert resiliently expanding to receive the rim in the recess, engage the inner flange with an inner surface of the rim, and engage the outer flange with an outer surface of the rim,
    wherein the insert includes a main body and the inner and outer flanges are provided at the perimeter of the main body, the plurality of orifices are provided in the main body and the inner and outer flanges are radially outward of the plurality of orifices, and
    wherein a cross sectional area of each orifice at an inner side of the vent insert is larger than a cross-sectional area of each orifice at an outer exit side of the vent insert, and the vent insert is insertable into the single opening in only a single orientation in which a smaller end of each orifice is positioned at the outer exit side of the vent insert.

5. The method of claim 4, wherein each orifice in the vent insert is larger on an inside of the mask than on an outside of the mask.

6. The method of claim 4, wherein squeezing the vent insert includes squeezing the vent insert about an axis that is substantially transverse to its longitudinal axis.

7. The method of claim 4, wherein the vent insert resiliently expands from a squeezed position to receive the rim in the recess.

8. The method of claim 4, wherein the inner flange of the vent insert is squeezed into the single opening, with the outer flange of the vent insert on top of the single opening, and part of the rim is received in the recess between the inner and outer flanges.

9. The method of claim 4, wherein the vent insert includes an elongated, non-circular shape.

10. The method of claim 4,
    wherein squeezing the vent insert includes squeezing the vent insert about an axis that is substantially transverse to its longitudinal axis,
    wherein the vent insert resiliently expands from a squeezed position to receive the rim in the recess,
    wherein the inner flange of the vent insert is squeezed into the single opening, with the outer flange of the vent insert on top of the single opening, and part of the rim is received in the recess between the inner and outer flanges, and
    wherein the vent insert includes an elongated, non-circular shape.

11. The method of claim 4, wherein the outer flange of the insert, as seen in cross-section, includes first and second flange portions on opposing sides of the insert to receive the rim on opposing sides of the single opening, and the first and second flange portions on each side of the insert extend a substantially equal distance from the single opening.

12. The method of claim 4, wherein the vent insert is structured to continuously exhaust gas in the range of 4-18 $cmH_2O$.

13. A method for attaching a washout vent insert to a CPAP mask, the CPAP mask comprised of a shell having an inlet tube, the CPAP mask comprising polycarbonate material, the shell having only a single opening for purposes of $CO_2$ washout, the single opening being bounded by a rim of said polycarbonate material, the vent insert constructed and arranged to be more flexible than the polycarbonate material of the rim, the vent insert having a plurality of orifices to continuously exhaust $CO_2$-laden gas from the CPAP mask during the entire breathing cycle of a patient while reducing noise generated by gas washout, the vent insert, in a cross-sectional view, having an inner flange and an outer flange, the inner and outer flanges defining a recess therebetween at a periphery of the vent insert, the method comprising:

squeezing the vent insert;

aligning the vent insert so it is oriented to match the shape of the single opening in the CPAP mask;

inserting the inner flange of the vent insert into the single opening; and releasing the vent insert once the inner flange is within the single opening, the vent insert resiliently expanding to receive the rim in the recess, engage the inner flange with an inner surface of the rim, and engage the outer flange with an outer surface of the rim, wherein an outer end of each orifice at an outer side of the insert is positioned outward of the outer surface of the rim, wherein the insert includes a main body and the inner and outer flanges are provided at the perimeter of the main body, the plurality of orifices are provided in the main body and the inner and outer flanges are radially outward of the plurality of orifices, wherein the recess of the vent insert and the single opening have non-circular, complementary shapes, and wherein a cross-sectional area of each orifice at an inner entry side of the vent insert is larger than a cross-sectional area of each orifice at an outer exit side of the vent insert, and the vent insert is insertable into the single opening in only a single orientation in which a smaller end of each orifice is positioned at the outer exit side of the vent insert.

14. The method of claim 13, wherein the shell is formed from a relatively more rigid material and a region surrounding or adjacent the plurality of orifices is formed from a relatively more flexible material compared to the relatively more rigid material.

15. The method of claim 13, wherein the outer flange of the insert, as seen in cross-section, includes first and second flange portions on opposing sides of the insert to receive the rim on opposing sides of the single opening, and the first and second flange portions on each side of the insert extend a substantially equal distance from the single opening.

16. The method of claim 13, wherein the vent insert is structured to continuously exhaust gas in the range of 4-18 $cmH_2O$.

17. A method for attaching a washout vent insert to a CPAP mask, the CPAP mask comprised of a main body having a shell having an inlet tube, the main body having only a single opening for purposes of $CO_2$ washout, the single opening being bounded by a rim, the vent insert having a plurality of orifices to continuously exhaust $CO_2$-laden gas from the CPAP mask during the entire breathing cycle of a patient, the vent insert having an inner flange and an outer flange, the inner and outer flanges defining a recess therebetween at a periphery of the vent insert, the method comprising:

temporarily flexing or deforming the vent insert to allow the inner flange to enter into the single opening; and releasing the vent insert once the inner flange is within the single opening to allow the vent insert to return to an unflexed or undeformed position to receive the rim in the recess, engage the inner flange with an inner surface of the rim, and engage the outer flange with an outer surface of the rim, thereby securing the vent insert relative to the rim, wherein the recess of the vent insert and the single opening have non-circular, complementary shapes, wherein the vent insert is structured and configured to reduce noise during gas washout, wherein a cross-sectional area of each orifice at an inner entry side of the vent insert is larger than a cross-sectional area of each orifice at an outer exit side of the vent insert, and wherein the vent insert is insertable into the single opening in only a single orientation in which a smaller end of each orifice is positioned at the outer exit side of the vent insert.

18. The method of claim 17, wherein temporarily flexing or deforming the vent insert includes squeezing the vent insert.

19. The method of claim 18, wherein squeezing the vent insert includes squeezing the vent insert about an axis that is substantially transverse to its longitudinal axis.

20. The method of claim 17, further comprising aligning the vent insert so it is oriented to match the shape of the single opening.

21. The method of claim 17, wherein the inner flange of the vent insert is squeezed into the single opening, with the outer flange of the vent insert on top of the single opening, and part of the rim is received in the recess between the inner and outer flanges.

22. The method of claim 17, wherein temporarily flexing or deforming the vent insert includes squeezing the vent insert, wherein squeezing the vent insert includes squeezing the vent insert about an axis that is substantially transverse to its longitudinal axis, further comprising aligning the vent insert so it is oriented to match the shape of the single opening, and wherein the inner flange of the vent insert is squeezed into the single opening, with the outer flange of the vent insert on top of the single opening, and part of the rim is received in the recess between the inner and outer flanges.

23. The method of claim 17, wherein the outer flange of the insert, as seen in cross-section, includes first and second flange portions on opposing sides of the insert to receive the rim on opposing sides of the single opening, and the first and second flange portions on each side of the insert extend a substantially equal distance from the single opening.

24. The method of claim 17, wherein the vent insert is structured to continuously exhaust gas in the range of 4-18 $cmH_2O$.

* * * * *